US008915892B2

United States Patent
Klewinghaus

(10) Patent No.: US 8,915,892 B2
(45) Date of Patent: Dec. 23, 2014

(54) T-PIECE FOR CREATING TURBULENCE

(71) Applicant: Fresenius Medical Care Deutschland GmbH, Bad Homburg (DE)

(72) Inventor: Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/962,050

(22) Filed: Aug. 8, 2013

(65) Prior Publication Data

US 2014/0050614 A1 Feb. 20, 2014

Related U.S. Application Data

(60) Provisional application No. 61/683,818, filed on Aug. 16, 2012.

(30) Foreign Application Priority Data

Aug. 16, 2012 (DE) .......................... 10 2012 016 210

(51) Int. Cl.
| | |
|---|---|
| *A61M 5/00* | (2006.01) |
| *A61M 25/00* | (2006.01) |
| *A61M 1/34* | (2006.01) |
| *A61M 1/36* | (2006.01) |
| *B01F 5/04* | (2006.01) |
| *B01F 5/06* | (2006.01) |
| *B01F 3/08* | (2006.01) |
| *A61M 39/00* | (2006.01) |

(52) U.S. Cl.
CPC ............... *A61M 1/34* (2013.01); *A61M 1/3472* (2013.01); *A61M 1/3621* (2013.01); *A61M 1/3672* (2013.01); *B01F 5/0473* (2013.01); *A61M 1/367* (2013.01); *B01F 5/0615* (2013.01); *B01F 3/0865* (2013.01); *A61M 1/342* (2013.01); *A61M 2039/0027* (2013.01); *A61M 2206/14* (2013.01); *B01F 2005/0636* (2013.01)
USPC .............................. 604/246; 604/284; 604/19

(58) Field of Classification Search
USPC ........... 604/4.01–6.16, 27, 30, 533, 537, 264, 604/284; 422/44–48
See application file for complete search history.

(56) References Cited

U.S. PATENT DOCUMENTS

| | | | | |
|---|---|---|---|---|
| 3,969,037 | A * | 7/1976 | Steiner .......................... | 416/176 |
| 6,120,008 | A | 9/2000 | Littman et al. | |
| 6,398,955 | B1 | 6/2002 | Fumiyama et al. | |
| 7,293,603 | B2 * | 11/2007 | Cox .............................. | 165/156 |
| 2009/0105630 | A1 | 4/2009 | Huang et al. | |
| 2011/0276024 | A1 * | 11/2011 | Randolph et al. ............. | 604/500 |

FOREIGN PATENT DOCUMENTS

| | | |
|---|---|---|
| WO | WO 2009/030973 | 3/2009 |
| WO | WO 2009030973 A1 * | 3/2009 |

\* cited by examiner

*Primary Examiner* — Philip R Wiest
*Assistant Examiner* — Benjamin Klein
(74) *Attorney, Agent, or Firm* — Jacobson Holman Hershkovitz, PLLC.

(57) ABSTRACT

Extracorporeal blood treatment methods are usually performed with anticoagulation of the blood. In regional anticoagulation with citrate, sometimes a blood clot is observed in the extracorporeal circulation at the point of addition of the calcium substitution solution. In such a case, the treatment must be interrupted. To prevent such an interruption, the point of addition is configured as a T-piece having a spiral structure for generating turbulence.

20 Claims, 4 Drawing Sheets

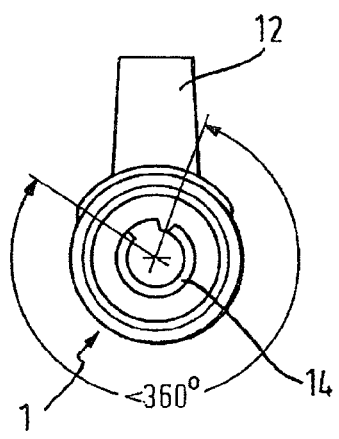 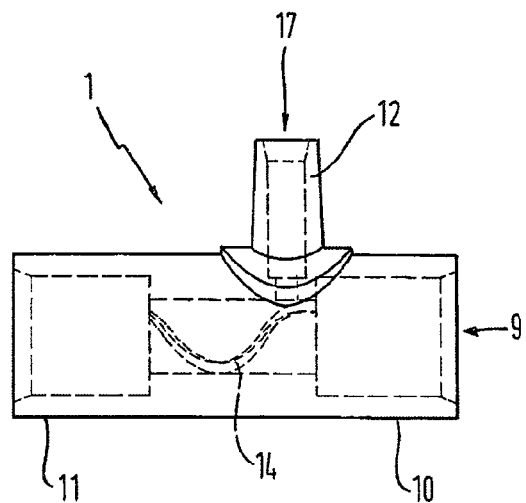
Fig. 4                    Fig. 5

T-PIECE FOR CREATING TURBULENCE

BACKGROUND OF THE INVENTION

1. Field of Invention

The invention relates to a T-piece having means for creating turbulence.

2. Description of the Prior Art

WO 2009/030973 describes a blood tubing system having an infusion site which in turn has a constriction, said constriction serving to create turbulence in this infusion site.

Statement of Problem

In extracorporeal blood treatment methods, blood is taken from the patient, then harmful substances are withdrawn from the blood by a treatment device, e.g., a dialysis filter, in an extracorporeal circulation, and then the treated blood is returned to the patient. To prevent occlusion of the blood tubing system and the treatment device used for this purpose due to blood clots, anticoagulant measures must be taken.

Mainly two methods are used for this purpose, namely systematic anticoagulation and regional anticoagulation. In systematic anticoagulation, a heparin solution is added through a T-piece to the blood in the blood tubing system as close to the arterial puncture needle as possible. In regional anticoagulation, a citrate solution capable of complexing calcium is used as the anticoagulant, which interrupts the coagulation cascade. Citrate and with the calcium bound to it are removed from the blood in the dialysis filter. When blood is returned to the patient in this method, the physiological calcium concentration must be restored because otherwise there may be adverse effects. Therefore, in regional anticoagulation, a solution containing calcium is added to the blood near the patient's venous access, thereby restoring the physiological blood calcium concentration.

T-pieces may be provided in the blood tubing system for adding infusion solutions to blood in an extracorporeal circulation; these T-pieces may be connected to the anticoagulant solution in regional anticoagulation and may be connected to the calcium-based replacement solution. The flow rate of the solutions to be added is generally low in relation to the blood flow rate (e.g., 10 mL/h up to 100 mL/min).

Because of the circular cross section and the smooth inside wall at the addition site, laminar flow conditions prevail inside the T-piece. These largely laminar flow conditions result in poor mixing of the blood with the added solution. This inadequate mixing of the two liquids at the addition site is undesirable, especially in the case of adding the calcium solution to blood, and in isolated cases this may result in the formation of blood clots downstream.

To prevent this, rapid and homogeneous mixing of the added calcium solution with the blood is advantageous.

The object of the present invention is to provide a T-piece, which ensures rapid and homogeneous mixing of the two liquids combined in the T-piece.

According to the teaching of the present invention, this object is achieved an insert piece having a main line for transporting a first liquid, the main line leading from a first connection point via an intermediate piece having a largely cylindrical inside wall to a second connection point, and a second line for metered addition of a second liquid to the first liquid, the second line leading from a third connection point to a mouth in the intermediate piece of the main line, the intermediate piece of the main line having a three-dimensional spiral structure for generating turbulence. The object is also achieved by a blood tubing system having the insert piece, and an arrangement having the insert piece, with the first and the second connection points being connected to a blood-carrying line of a blood tubing system for producing an extracorporeal circulation for a blood treatment method, and the third connection point being connected to a line to an electrolyte solution. Advantageous embodiments of the invention are described herein.

SUMMARY OF THE INVENTION

The present invention consists of an insert piece, e.g., a T-piece for a bloodline system having a main line for transporting a first liquid, preferably blood. The main line consists of a first connection point, which leads to a second connection point by way of an intermediate piece having a largely cylindrical inside wall.

In addition, the insert piece has a second line for metered addition of a second liquid to the first liquid, said line leading from a third connection point to a mouth in the intermediate piece in the main line. The intermediate piece in the main line has a three-dimensional spiral structure for creating turbulence.

The three-dimensional spiral structure may be designed as an elevated bulge on the inside wall of the intermediate piece.

As an alternative to that the three-dimensional spiral structure may also be embodied as a recessed cutout in the inside wall of the intermediate piece.

The spiral structure may be designed to be trapezoidal. Alternatively, the spiral structure may have a sickle-shaped design.

The spiral structure may be designed as a single-start spiral structure, such that in a preferred embodiment, the single-start spiral structure rotates around the inside wall at an angle of less than 360°. This has advantages in fabrication of the injection mold for producing the insert piece in particular.

As an alternative to this, the three-dimensional spiral structure may also be embodied as a multi-start spiral structure.

In another embodiment, the insert piece may also be designed in two parts. Then the three-dimensional spiral structure consists of a curved wire type material which may be inserted or glued into the insert piece.

To achieve the most thorough and most efficient possible mixing, the mouth of the second line in a preferred embodiment is situated in the upstream half of the intermediate piece. The mouth of the second line should be located as close as possible to the connection point at the inlet of the insert piece. The mouth of the second line should be located as close as possible to the spiral structure. The first and second liquids are thus guided through the device for creating turbulence for the greatest possible distance and are thus mixed especially efficiently.

In a particularly preferred embodiment, the mouth is situated next to the downstream flank of the bulge. Then the mouth is not arranged symmetrically between two bulges but instead is offset asymmetrically to the downstream flank.

In a preferred embodiment, the connection points are designed with a tube seating.

The invention also relates to a blood tubing system for producing an extracorporeal circulation for a blood treatment method having at least one insert piece according to as described herein. This blood tubing system may be suitable for performing hemodialysis, hemofiltration or hemodiafiltration. The blood tubing system would then comprise a first arterial line for withdrawing blood, said line leading to a blood filter. The blood filter may be supplied separately but may also be preconnected to the tubing system. The blood filter may be a dialysis filter, a filter for hemofiltration of a filter for plasmapheresis or whole-blood adsorption. One end of the first arterial line may be provided with a withdrawal cannula while the second and is connected to the blood filter. An insert in the form of a T-piece which serves to introduce an anticoagulant into the blood may also be provided in this line segment A preferred embodiment may relate to an insert as described herein. In additional the conventional components of a blood tubing system such as a drip chamber or inserts for the blood pumps may be provided. Then a second venous line would lead back to the patient from the blood filter. In a preferred embodiment, the insert described herein would be inserted into the venous line returning to the patient. The venous line leading from the blood filter to the patient would then consist of two segments. The first venous segment is connected to the blood filter at one end and at the other end is connected to the first connection point, the inlet of the insert piece. The tube is preferably glued into the seating of the tubing of the insert piece. The second venous line segment would then be connected to the second connection point, the outlet of the insert piece. This is also preferably glued into the tube seating of the insert piece. The third connection point of the insert piece is connected to a third line. This line is glued into the tubing seating on one end. The other end of the line may be provided with connecting means for an infusion solution. These connecting means may comprise a Luer connector, a cannula, a spike or the like. In a preferred embodiment, the infusion solution serves to restore the physiological ionic concentration of the blood. It may be used for replacement of the calcium content of the blood, for example, which is reduced due to regional anticoagulation.

The second venous line may additionally comprise the components that are customary in blood tubing systems and are familiar to those skilled in the art, such as a drip chamber, additional insert pieces in the T-pieces or injection points, etc.

In a preferred embodiment, the blood tubing system is suitable for performing an extracorporeal blood treatment using regional anticoagulation.

In addition, the invention relates to an arrangement having an insert piece as described herein, wherein the first and the second connection points are connected to a blood-carrying line of the blood tubing system, and the third connection point is connected to a line to a physiological electrolyte solution. In a preferred embodiment, the physiological electrolyte solution is a solution restoring the physiological calcium concentration. The arrangement described here thus relates to a treatment set for regional anticoagulation.

BRIEF DESCRIPTION OF THE DRAWINGS

Further details and advantages of the invention are now described in greater detail on the basis of the exemplary embodiments depicted in the drawings, where:

FIG. 4: shows a cross section through a third embodiment of the insert piece according to the invention;

FIG. 5: shows a longitudinal section through a third embodiment of an insert piece according to the invention with an upstream position of the third connection point.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
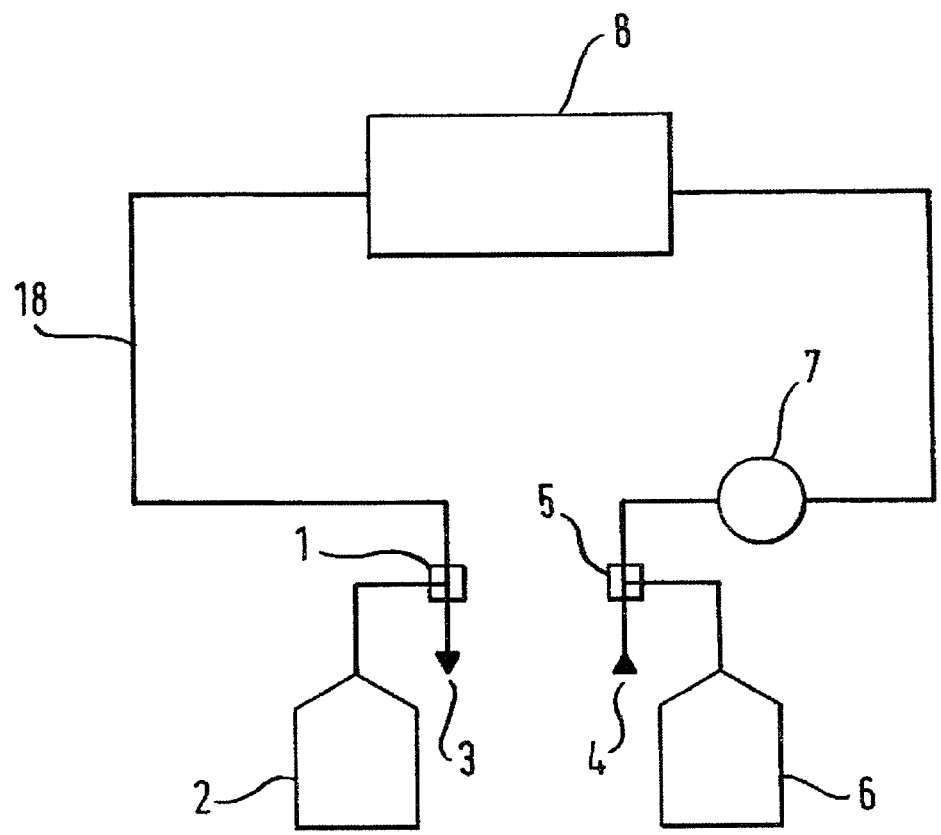
FIG. 1: shows a schematic diagram of an extracorporeal circulation having regional anticoagulation.

FIG. 1 shows schematically an extracorporeal circulation with regional anti-coagulation. Blood is withdrawn from the patient's arterial access 4 and pumped by the blood pump 7 into the blood tubing system 18 of the extracorporeal circulation. A T-piece 5 in which blood is anticoagulated with a citrate solution 6 is situated as close as possible to the patient's arterial access 4. The blood then passes through the dialysis filter 8, in which citrate and also complexed calcium to some extent are removed. Before returning to the patient through the patient's venous access 3, the blood is mixed with a calcium solution 2 in a T-piece 1, thus yielding a physiological blood composition.

Figure 2:
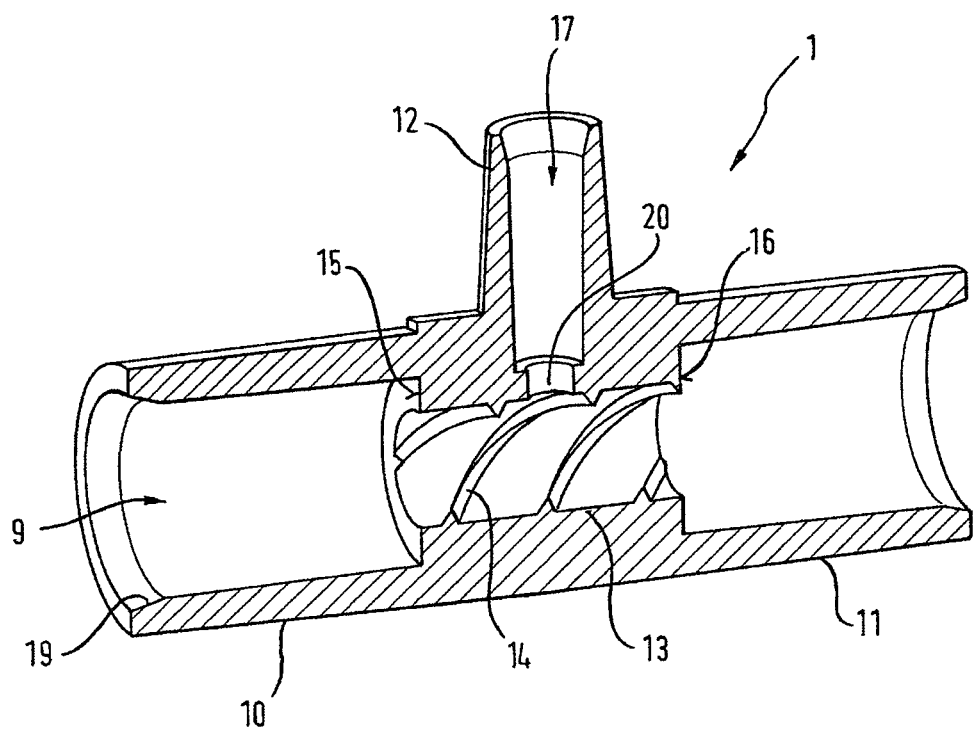
FIG. 2: shows a longitudinal section through a first embodiment of an insert piece according to the invention having a three-dimensional spiral structure.

FIG. 2 shows a longitudinal section through a first embodiment of the insert piece 1 according to the invention in the form of a T-piece. The insert piece 1 has a main line 9, which leads from a first connection point 10 to a second connection point 11 by way of an intermediate piece 13 having a cylindrical inside wall. The transitional points between the connection points 10 and 11 and the intermediate piece 13 each form a tube seating 15 and 16 for the blood tubing system 18 (not shown). To simplify the insertion of the blood tubing system into the connection points 10 and 11, they have an insertion chamfer 19. Furthermore, the insert piece 1 has a second line 17 leading from a third connection point 12 to a mouth 20 in the intermediate piece 13 in the main line 9. The intermediate piece 13 has a three-dimensional spiral structure 14 in the form of an elevated bulge on the inside wall. This spiral structure results in the creation of turbulence in the liquid conveyed in the main line. The liquid, e.g., a calcium solution, conveyed in the second line 17, which is connected via the third connection point 12 to the intermediate piece of the main line, is therefore mixed more rapidly with the liquid in the main line 9.

Figure 3:
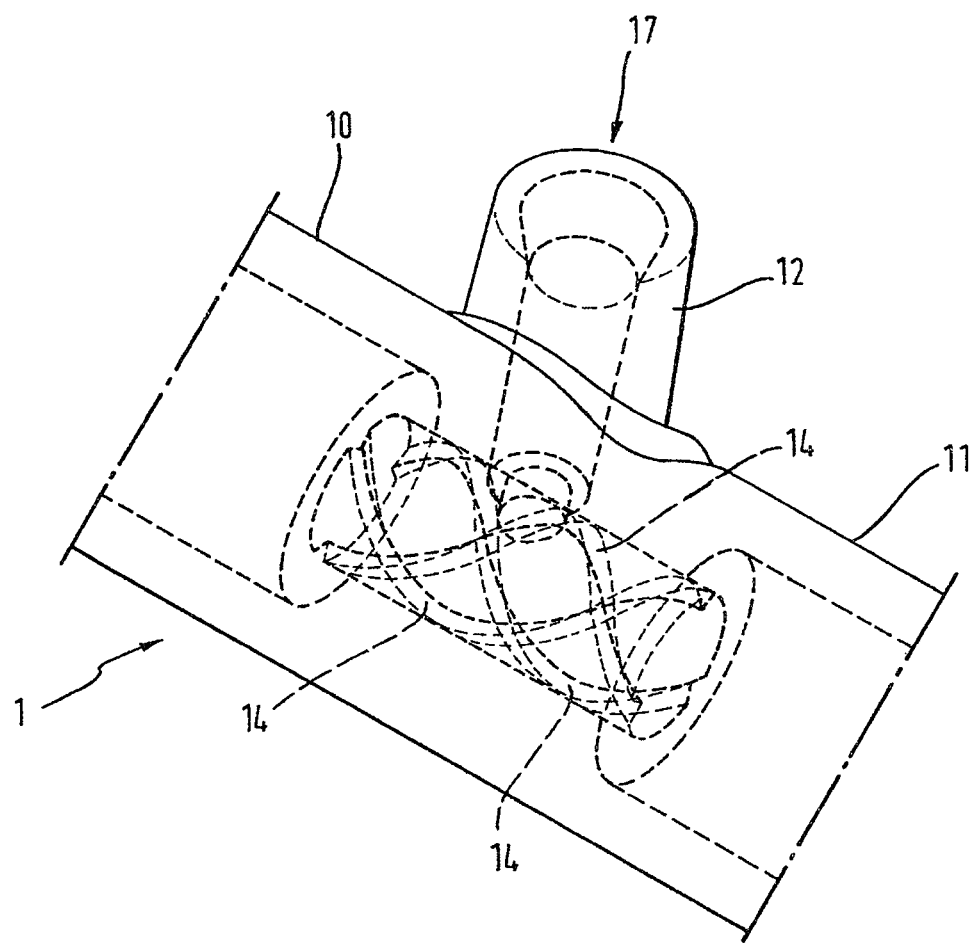
FIG. 3: shows a perspective view of a second embodiment of an insert piece according to the invention having a single-start spiral structure.

FIG. 3 shows a second embodiment of an insert piece 1 according to the invention in a multi-start spiral structure. The intermediate piece 13 has three elevated bulges 14 running in a spiral on the inside wall.

FIG. 4 shows a cross section through a third embodiment of the insert piece 1. The wrap-around angle of the spiral bulge 14 amounts to less than 360°. The insert piece is thus simple to produce in terms of the injection molding technology and nevertheless a sufficient turbulence is created.

FIG. 5 shows a longitudinal section through a third embodiment of the insert piece 1. The mouth 20 is arranged as close as possible to the spiral structure 14 upstream in the intermediate piece 13. Blood in the main line 9 is thus optimally mixed with the calcium solution, which is added through the second line 17. Furthermore, the mouth of the line 17 is situated next to the downstream flank of the bulge 14 because of the more favorable turbulence and pressure conditions.

In any extracorporeal circulation, the blood compatibility must also be taken into account in addition to possible coagulation. Cells that are sensitive to the mechanical stresses in circulation must be minimized in the blood as much as possible. The blood is exposed to high shearing forces at constriction points, which should be avoided if at all possible, in the blood tubing system.

In the T-piece according to the invention, the diameter of the inside wall of the intermediate piece is designed to correspond to the diameter of the blood tubing system. Blood in the T-piece, where turbulence is generated due to the spiral structure, is hardly exposed to any shearing forces at all. The device according to the invention is thus especially hemocompatible.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An insert piece for a tubing system, said insert piece comprising:
   a main line for transporting a first liquid, the main line leading from a first connection point via an intermediate piece having a substantially cylindrical inside wall to a second connection point; and
   a second line for metered addition of a second liquid to the first liquid, the second line leading from a third connection point to a mouth in the intermediate piece,
   the intermediate piece including, for generating turbulence so as to mix the first and the second liquids, a three-dimensional spiral structure configured as an elevated bulge on the inside wall thereof.

2. The insert piece according to claim 1, wherein the three-dimensional spiral structure further comprises a recessed cut-out in the inside wall of the intermediate piece.

3. The insert piece according to claim 1, wherein the three-dimensional spiral structure is trapezoidal-shaped or sickle-shaped.

4. The insert piece according to claim 1, wherein the three-dimensional spiral structure has a single-start configuration.

5. The insert piece according to claim 1, wherein the three-dimensional spiral structure extends around to the inside wall at an angle of less than 360°.

6. The insert piece according to claim 1, wherein the three-dimensional spiral structure has a multi-start configuration.

7. The insert piece accord to claim 1, wherein the three-dimensional spiral structure includes a curved wire-shaped material.

8. The insert piece according to claim 1, wherein the mouth of the second line is in an upstream half of the intermediate piece.

9. The insert piece according to claim 1, wherein the mouth of the second line is arranged next to a downstream flank of the elevated bulge.

10. The insert piece according to claim 1, wherein the first liquid is blood.

11. A blood tubing system for producing an extracorporeal circulation for a blood treatment method, said blood tubing system comprising:
    an insert piece including
    a main line for transporting a first liquid, the main line leading from a first connection point via an intermediate piece having a substantially cylindrical inside wall a second connection point; and
    a second line for metered addition to a second liquid to the first liquid, the second line leading from a third connection point to a mouth in the intermediate piece,
    the intermediate piece including, for generating turbulence so as to mix the first and the second liquids, a three-dimensional spiral structure configured as an elevated bulge on the inside wall thereof.

12. The blood tubing system according to claim 11, wherein the extracorporeal circulation is configured for performing hemodialysis, hemofiltration, hemodiafiltration, a plasmapheresis treatment, or a whole-blood adsorption treatment.

13. The blood tubing system according to claim 11, wherein the extracorporeal circulation is configured for performing a regional anticoagulation.

14. A system comprising:
    an insert piece including
    a main line for transporting a first liquid, the main line leading from a first connection point via an intermediate piece having a substantially cylindrical inside wall to a second connection point; and
    a second line for metered addition of a second liquid to the first liquid, the second line leading from a third connection point to a mouth in the intermediate piece,
    the intermediate piece including, for generating turbulence so as to mix the first and the second liquids, a three-dimensional spiral structure configured as an elevated bulge on the inside wall thereof
    the first and the second connection points being connected to a blood-carrying line of a blood tubing system for producing an extracorporeal circulation for a blood treatment method using said insert piece, and the third connection point being connected to a line to an electrolyte solution.

15. The system according to claim 14, wherein the electrolyte solution restores a physiological calcium concentration of blood.

16. An insert piece for a tubing system, said insert piece comprising:
    a first line for transporting a first liquid therethrough, the first line including a first connection point and a second connection point, and an intermediate piece located therebetween, the intermediate piece having a substantially cylindrical inside wall, with a wall opening located therein; and
    a second line including a third connection point, the second line being configured for metered addition therethrough of a second liquid to the first liquid via the wall opening in the intermediate piece,
    the intermediate piece including a three-dimensional spiral structure for generating turbulence and mixing the first and the second liquids, and
    the wall opening being provided in a half of the intermediate piece that is adjacent an inlet of the first fluid to the intermediate piece.

17. The insert piece according to claim 16, wherein the three-dimensional spiral structure is configured as an elevated protrusion arranged axially along the inside wall of the intermediate piece.

18. The insert piece according to claim 16, wherein the insert piece is substantially T-shaped, and wherein an interior diameter of the intermediate piece is smaller than an interior diameter of the first line.

19. The insert piece according to claim 16, wherein the wall opening is adjacent a downstream flank of the elevated protrusion so as to be asymmetrically offset relative thereto.

20. The insert piece according to claim 16, wherein the intermediate piece is axially oriented parallel to a longitudinal axis of the first line.

* * * * *